United States Patent [19]

Schmidt

[11] 4,420,629
[45] Dec. 13, 1983

[54] METHOD OF PREPARING 3-ALKYL-6-METHYL-β-RESORCYLIC ACID ESTERS

[75] Inventor: Hans-Georg Schmidt, Niederkassel-Ranzel, Fed. Rep. of Germany

[73] Assignee: Dynamit Nobel AG, Cologne, Fed. Rep. of Germany

[21] Appl. No.: 416,733

[22] Filed: Sep. 10, 1982

[30] Foreign Application Priority Data

Sep. 16, 1981 [DE] Fed. Rep. of Germany ....... 3136720

[51] Int. Cl.³ .............................................. C07C 69/88
[52] U.S. Cl. ................................................. 560/70
[58] Field of Search ......................................... 560/70

[56] References Cited

U.S. PATENT DOCUMENTS 3,944,596  3/1976  Cohen .................... 560/70

FOREIGN PATENT DOCUMENTS 902636  6/1972  Canada .................... 560/70

*Primary Examiner*—Paul J. Killos
*Attorney, Agent, or Firm*—Felfe & Lynch

[57] ABSTRACT

3-alkyl-6-methyl-β-resorcylic acid esters of the Formula

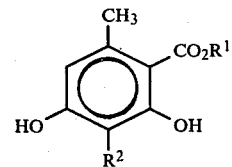

wherein $R^1$ and $R^2$ represent identical or different alkyl groups of 1 to 10 carbon atoms, are prepared by the reaction of α-pyrones of the formula

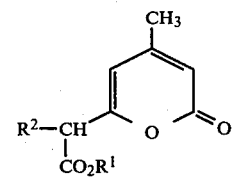

wherein $R^1$ and $R^2$ have the above meaning, with a base.

7 Claims, No Drawings

METHOD OF PREPARING 3-ALKYL-6-METHYL-β-RESORCYLIC ACID ESTERS

This invention relates to a process for the preparation of 3-alkyl-6-methyl-β-resorcylic acid esters. Such esters are useful as scents having "oak moss character."

There are several methods of preparing alkyl-substituted β-resorcylic acid esters from alkylated dihydro-β-resorcylic acid esters (DE-OS No. 2,653,177, BE Pat. No. 73.8046, NL Pat. No. 807,693).

The conversion to the aromatics is performed by oxidation methods (e.g., sulfuric acid, halogens). Another method of preparation consists in the transposition of malonic esters with α,β-unsaturated α-acyloxyalkenones in the presence of stoichiometric amounts of sodium hydride (U.S. Pat. No. 3,928,419). In all cases, the starting products are not easily accessible and the yields of the pure end product are low.

THE INVENTION

It is the object of the present invention to create a simplified process and use easily available starting products.

The subject matter of the invention is a method of preparing 3-alkyl-6-methyl-β-resorcylic acid esters of the formula

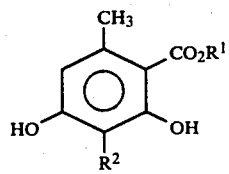

which is characterized in that an α-pyrone of the formula

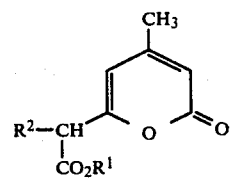

in which $R^1$ and $R^2$ can be identical or different, and represent alkyl moieties of 1 to 10 carbon atoms, is reacted with a base.

Preferred alkyl groups are those of 1 to 5 carbon atoms, especially methyl, ethyl, n- and i-propyl, n- and i-butyl.

Alkali or alkaline earth alcoholates, alkali or alkaline earth hydroxides or carbonates are preferred as bases. As a rule, first an alkali or alkaline earth resorcinate corresponding to Formula I is produced, from which the free 3-alkyl-6-methyl-β-resorcylic acid ester of Formula I is obtained.

The base is used preferably in stoichiometric or slightly more than stoichiometric amounts.

The reaction is preferably performed in a solvent such as alcohols, ethers etc. The reaction can be performed in a wide temperature range from +10° C. to 200° C. The reaction in the boiling solvent as standard pressure or at self-produced pressure is preferred.

The release of the recorcinols of General Formula I from the corresponding resorcinates can be performed with, for example, the equivalent amount of aqueous mineral acids or organic acids, such as acetic acid, for example. The isolation of the resorcinols of General Formula I is then accomplished preferably by extraction, and the purification by recrystallization.

The preparation of the starting compounds of General Formula II is described in German Offenlegungsschrift No. 2,916,648.

The present invention will be explained by the following examples:

EXAMPLES

Example 1

30 grams of 4-methyl-α-pyronyl-6-(α-isopropyl)-acetic acid methyl ester are dissolved in 150 ml of methanol and 10.8 grams of sodium methylate are added. Under an inert gas atmosphere, the mixture is refluxed for three hours and, after the solution has cooled, it is acidified with 2 N aqueous sulfuric acid solution. By extraction with ether, 24.3 g of 3-isopropyl-6-methyl-β-resorcylic acid methyl ester is obtained. After recrystallization from chloroform, it is in the form of colorless crystals (M.P. 144°-145° C.).

Example 2

5.0 grams of sodium methylate in 70 ml of methanol are added to 12 grams of 4-methyl-α-pyronyl-6-(α-methyl)-acetic acid methyl ester and this mixture is refluxed for 3 hours. Then the procedure of Example 1 is followed. 9.6 grams of 3,6-dimethyl-β-resorcylic acid methyl ester are obtained having, after recrystallization from water, a melting point of 142°-144° C.

It will be understood that the specification and examples are illustrative but not limitative of the present invention and that other embodiments within the spirit and scope of the invention will suggest themselves to those skilled in the art.

What is claimed is:

1. Process of preparing 3-alkyl-6-methyl-β-resorcylic acid esters of the formula

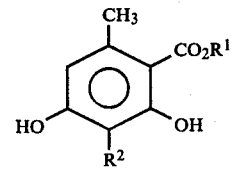

wherein $R^1$ and $R^2$ are individually select from alkyl groups from 1 to 10 carbon atoms which process comprises reacting an alpha-pyrone of the formula

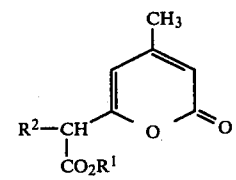

wherein $R^1$ and $R^2$ are identified as above with a base, to result in the desired ester compound.

2. Process as claimed in claim 1, wherein the free 3-alkyl-6-methyl-β-resorcylic acid ester is isolated from the salt-form reaction mixture, by acidifying the reaction mixture with at least one acid.

3. Process as claimed in claim 1, wherein the said base is an alcoholate of an alkali or alkaline earth metal.

4. Process as claimed in claim 1, wherein the said base is a hydroxide of an alkali or alkaline earth metal.

5. Process as claimed in claim 1, wherein the said base is a carbonate of an alkali or alkaline earth metal.

6. Process as claimed in claim 1, wherein the reaction is performed at a temperature of from 10° to 200° C.

7. Process as claimed in claim 1, wherein the reaction is carried out in a solvent.

* * * * *